US012758325B2

(12) United States Patent
Barbagli et al.

(10) Patent No.: US 12,758,325 B2
(45) Date of Patent: Oct. 13, 2026

(54) SYSTEMS AND METHODS FOR ENTRY POINT LOCALIZATION

(71) Applicant: INTUITIVE SURGICAL OPERATIONS, INC., Sunnyvale, CA (US)

(72) Inventors: Federico Barbagli, San Francisco, CA (US); Lisa Ison, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 33 days.

(21) Appl. No.: 18/949,480

(22) Filed: Nov. 15, 2024

(65) Prior Publication Data

US 2025/0064532 A1 Feb. 27, 2025

Related U.S. Application Data

(63) Continuation of application No. 18/452,385, filed on Aug. 18, 2023, now Pat. No. 12,171,505, which is a (Continued)

(51) Int. Cl.
*A61B 34/20* (2016.01)
*A61B 17/34* (2006.01)
(Continued)

(52) U.S. Cl.
CPC .......... *A61B 34/20* (2016.02); *A61B 17/3423* (2013.01); *A61B 34/35* (2016.02);
(Continued)

(58) Field of Classification Search
CPC ......... A61B 34/20; A61B 34/35; A61B 34/37; A61B 17/3423; A61B 90/13;
(Continued)

(56) References Cited

U.S. PATENT DOCUMENTS 6,288,783 B1 9/2001 Auad
6,380,732 B1 4/2002 Gilboa
(Continued)

FOREIGN PATENT DOCUMENTS

WO WO-2016029289 A1 3/2016
WO WO-2016064632 A1 4/2016
(Continued)

OTHER PUBLICATIONS

Extended European Search Report for Application No. EP17857549.4, mailed on Apr. 29, 2020, 10 pages.
(Continued)

*Primary Examiner* — Ryan J. Severson
(74) *Attorney, Agent, or Firm* — Haynes & Boone, LLP.

(57) ABSTRACT

A method performed by a computing system includes determining an entry position and entry vector of an entry port in a surgical coordinate space, the entry port providing a passageway for insertion of a first medical instrument into a patient's body, wherein the determining of the entry position and entry vector occurs while the first medical instrument is external to the entry port; positioning the first medical instrument based on the entry position and the entry vector of the entry port; and advancing a distal end of the first medical instrument into the entry port.

20 Claims, 12 Drawing Sheets

Related U.S. Application Data continuation of application No. 17/538,047, filed on Nov. 30, 2021, now Pat. No. 11,779,405, which is a continuation of application No. 16/331,713, filed as application No. PCT/US2017/054483 on Sep. 29, 2017, now Pat. No. 11,219,490.

(60) Provisional application No. 62/402,625, filed on Sep. 30, 2016.

(51) Int. Cl.

*A61B 34/35* (2016.01)
*A61B 34/37* (2016.01)
*A61B 34/30* (2016.01)
*A61B 90/00* (2016.01)
*A61B 90/13* (2016.01)

(52) U.S. Cl.

CPC ...... *A61B 34/37* (2016.02); *A61B 2034/2051* (2016.02); *A61B 2034/2055* (2016.02); *A61B 2034/2059* (2016.02); *A61B 2034/2061* (2016.02); *A61B 2034/301* (2016.02); *A61B 2090/061* (2016.02); *A61B 90/13* (2016.02); *A61B 2090/3937* (2016.02)

(58) Field of Classification Search

CPC .... A61B 2034/2051; A61B 2034/2055; A61B 2034/2059; A61B 2034/2061; A61B 2034/301; A61B 2090/061; A61B 2090/3937

See application file for complete search history.

(56) References Cited

U.S. PATENT DOCUMENTS 6,389,187 B1 5/2002 Greenaway et al.
6,676,669 B2 1/2004 Charles et al.
7,316,681 B2 1/2008 Madhani et al.
7,625,383 B2 12/2009 Charles et al.
7,772,541 B2 8/2010 Froggatt et al.
7,781,724 B2 8/2010 Childers et al.
7,892,243 B2 2/2011 Stuart et al.
8,900,131 B2 12/2014 Chopra et al.
9,066,737 B2 * 6/2015 Barwinkel ............. A61B 34/30
9,259,274 B2 2/2016 Prisco
9,285,246 B2 * 3/2016 Prisco ................. H04L 63/0807
9,452,276 B2 9/2016 Duindam et al.
9,730,611 B2 * 8/2017 Kowshik ................ A61B 34/20
9,737,371 B2 * 8/2017 Romo .................... A61B 34/30
10,111,678 B2 10/2018 Jinno et al.
10,499,999 B2 * 12/2019 Yu .......................... A61B 34/30
11,219,490 B2 1/2022 Barbagli et al.
11,278,354 B2 * 3/2022 Duindam ............. A61B 1/2676
11,399,895 B2 * 8/2022 Soper ..................... A61B 34/20
11,779,405 B2 10/2023 Barbagli et al.
12,171,505 B2 * 12/2024 Barbagli ................ A61B 34/35
2002/0030483 A1 * 3/2002 Gilboa .................. G01S 13/874 324/207.17
2002/0133174 A1 * 9/2002 Charles .................. A61B 34/70 606/130
2006/0013523 A1 1/2006 Childlers et al.
2006/0030841 A1 * 2/2006 Madhani ................ A61B 34/77 606/1
2007/0065077 A1 * 3/2007 Childers ............ G01D 5/35354 385/12
2007/0250078 A1 * 10/2007 Stuart .................... A61B 34/20 606/130
2008/0212082 A1 * 9/2008 Froggatt .............. G01D 5/3539 356/73.1
2009/0281452 A1 11/2009 Pfister et al.
2010/0082041 A1 * 4/2010 Prisco .................... A61B 34/30 606/130
2011/0202069 A1 8/2011 Prisco et al.
2012/0226145 A1 9/2012 Chang et al.
2012/0289777 A1 * 11/2012 Chopra ................ A61B 5/6852 382/128
2013/0066335 A1 3/2013 Barwinkel et al.
2013/0096377 A1 * 4/2013 Duindam ............... A61B 1/009 600/104
2014/0051987 A1 2/2014 Kowshik et al.
2016/0100896 A1 4/2016 Yu
2016/0100898 A1 * 4/2016 Jinno ..................... A61B 17/29 606/130
2016/0184032 A1 6/2016 Romo et al.
2017/0165005 A1 6/2017 Kheradpir et al.
2017/0252548 A1 9/2017 Krimsky
2018/0256262 A1 9/2018 Duindam et al.
2019/0038365 A1 2/2019 Soper et al.
2019/0269470 A1 * 9/2019 Barbagli ............ A61B 17/3423
2022/0079689 A1 * 3/2022 Barbagli ................ A61B 34/20
2023/0389998 A1 12/2023 Barbagli et al.
2025/0064532 A1 * 2/2025 Barbagli ................ A61B 34/37

FOREIGN PATENT DOCUMENTS

WO WO-2016082018 A1 6/2016
WO WO-2016116753 A1 7/2016

OTHER PUBLICATIONS

International Preliminary Report on Patentability for Application No. PCT/US2017/054483, mailed on Apr. 11, 2019, 11 pages (ISRG08430/PCT).

International Search Report and Written Opinion for Application No. PCT/US2017/054483, mailed on Jan. 9, 2018, 15 pages (ISRG08430/PCT).

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR ENTRY POINT LOCALIZATION

RELATED APPLICATIONS

This patent application is a continuation of U.S. patent application Ser. No. 18/452,385, filed Aug. 18, 2023, which is a continuation of U.S. patent application Ser. No. 17/538,047, filed Nov. 30, 2021, which is a continuation of U.S. patent application Ser. No. 16/331,713, filed Mar. 8, 2019, which is the U.S. national phase of International Application No. PCT/US2017/054483, filed Sep. 29, 2017, which designated the U.S. and claims priority to and the benefit of the filing date of U.S. Provisional Patent Application No. 62/402,625, entitled "SYSTEMS AND METHODS FOR ENTRY POINT LOCALIZATION," filed Sep. 30, 2016, all of which are incorporated by reference herein in their entirety.

FIELD

The present disclosure is directed to systems and methods for navigating a medical instrument into an entry point of a patient, and more particularly to systems and methods for localizing the entry point.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Such natural orifices or surgically created incisions are referred to as entry points. Through these entry points, clinicians may insert minimally invasive medical instruments (including surgical, diagnostic, therapeutic, or biopsy instruments) to reach a target tissue location. Various techniques may be used to identify the precise position of a portion of the medical instrument in space. For example, a computing system may receive data from sensors associated with the medical instrument. The computing system may then analyze that data to determine a point in space in which the medical instrument is currently positioned with respect to a reference fixture.

In some examples, multiple medical instruments may be inserted through the entry point. For example, an outer catheter, an inner catheter, and a medical tool may be separated controlled and to move with respect to each other and to be inserted through the entry point. Specifically, the inner catheter may move within the outer catheter. The medical tool may move within the inner catheter. In such systems it is desirable to use methods and systems that improve the movement of such systems with respect to the patient to provide improved use of the medical instruments.

SUMMARY

The embodiments of the invention are summarized by the claims that follow the description. According to one example, a method performed by a computing system comprises determining an entry position and entry vector of an entry port in a surgical coordinate space. The entry port provides a passageway for insertion of a first medical instrument into a patient's body. The determination of the entry position and entry vector occurs while the first medical instrument is external to the entry port. The method also comprises positioning the first medical instrument based on the entry position and the entry vector of the entry port and advancing a distal end of the first medical instrument along the entry vector into the entry port.

According to another example, a method performed by a computing system comprises determining an entry position of an entry port in a surgical coordinate space based on a sensor assembly disposed on the entry port. The entry port providing a passageway for insertion of a first medical instrument into a patient's body. The method also comprises positioning a teleoperational manipulator, to which the first medical instrument is coupled, based on the entry position and advancing a distal end of a first medical instrument into the entry port.

According to another example, a teleoperative system comprises a teleoperational manipulator; a flexible medical instrument coupled to and movable by the teleoperational manipulator; and an entry port providing a passageway for insertion of the medical instrument into a patient body. The system also comprises a sensor system including a first sensor coupled to the entry port and a control system configured to use information from the first sensor to determine a position and orientation of the entry port with respect to the flexible medical instrument.

According to another example, a teleoperative system comprises a first medical instrument connected to and movable by a first manipulator assembly and a second medical instrument connected to and movable by a second manipulator assembly. The second medical instrument sized and shaped to fit and move within the first medical instrument The system further comprises a first alignment component positioned on one of the first manipulator assembly and the second manipulator assembly, a second alignment component positioned on an entry port, and a control system configured to use the first and second alignment components to determine a position and orientation of the entry port with respect to a position of the second medical instrument.

According to another example, a teleoperative system comprises a first medical instrument connected to and movable by a first manipulator assembly and a second medical instrument connected to and movable by a second manipulator assembly. The second medical instrument sized and shaped to fit and move within the first medical instrument. The system further comprises an alignment component positioned on an entry port and a control system configured to use the alignment component to determine a position of the entry port with respect to a position of the second medical instrument.

According to another example, a method performed by a computing system comprises positioning a distal end of a medical instrument at a first position within an entry port in a surgical coordinate space. The entry port provides a passageway for insertion of a medical instrument into a patient's body. The method also includes recording a first position of the distal end of the medical instrument in response to a fiber-optic shape sensor of the medical instrument passing by a temperature anomaly device on the entry port and positioning the distal end of the medical instrument at a second position within the entry port. The method also includes recording a second position of the distal end of the medical instrument in response to the fiber-optic shape sensor of the medical instrument passing by the temperature anomaly device on the entry port. The method also includes determining an entry position and entry vector of the entry port from the recorded first and second positions and positioning the first medical instrument based on the entry position and the entry vector of the entry port. The method also includes advancing a distal end of the medical instrument along the entry vector into the entry port.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
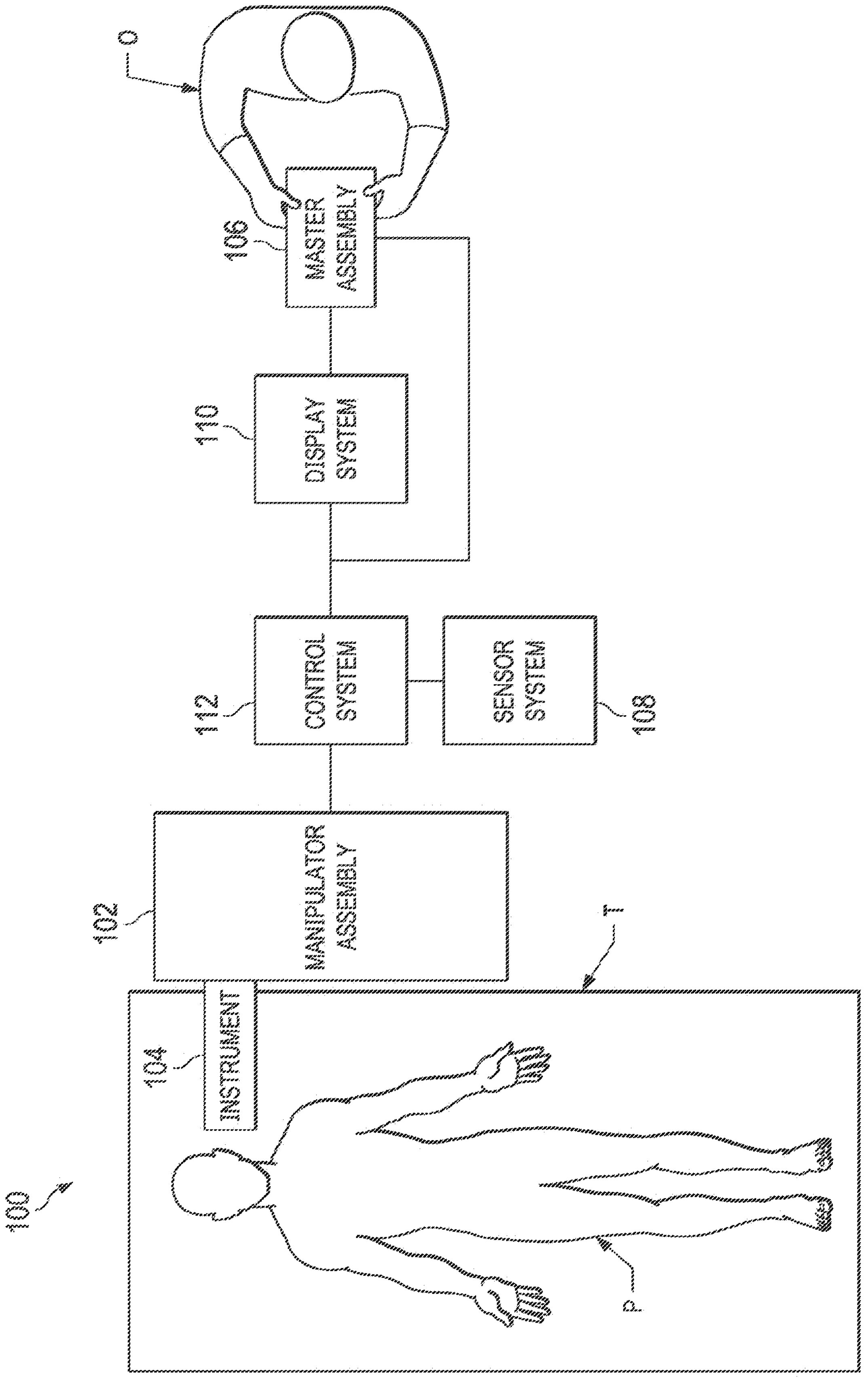
FIG. 1 illustrates a teleoperative medical system, according to one example of the present disclosure.

Referring to FIG. 1 of the drawings, a teleoperated medical system for use in, for example, surgical, diagnostic, therapeutic, or biopsy procedures, is generally indicated by the reference numeral 100. As shown in FIG. 1, the teleoperated system 100 generally includes a teleoperational manipulator assembly 102 for operating a medical instrument 104 in performing various procedures on the patient P. The assembly 102 is mounted to or near an operating tableT. A master assembly 106 allows an operator O (e.g., a clinician, a physician, a surgeon, or a user) to view the interventional site and to control the slave manipulator assembly 102.

The master assembly 106 may be located at an operator's console which is usually located in the same room as operating table T. However, it should be understood that the operator O can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated medical instruments 104 to provide the operator with telepresence, or the perception that the control devices are integral with the instruments 104 so that the operator has a strong sense of directly controlling instruments 104. In other embodiments, the control devices may have more or fewer degrees of freedom than the associated medical instruments 104 and still provide the operator with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes a plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the clinician or operator O. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the operator's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments often for purposes of imaged guided surgical procedures, the display 110 may display a virtual navigational image in which the actual location of the medical instrument 104 is registered (i.e., dynamically referenced) with the preoperative or concurrent images/model to present the clinician or operator O with a virtual image of the internal surgical site from the viewpoint of the location of the tip of the instrument 104. An image of the tip of the instrument 104 or other graphical or alphanumeric indicators may be superimposed on the virtual image to assist the operator controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or operator O with a virtual image of medical instrument within the surgical site from an external viewpoint. An image of a portion of the medical instrument or other graphical or alphanumeric indicators may be superimposed on the virtual image to assist the operator controlling the instrument 104.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein, including instructions for providing registered images to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104 when used in an image-guided surgical procedure. Virtual navigation using the virtual visualization system is based upon reference to the acquired preoperative or intraoperative dataset of the anatomic passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively at a prior time during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using electromagnetic (EM) sensor, fiber-optic sensors, or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figures 2A, 2B:
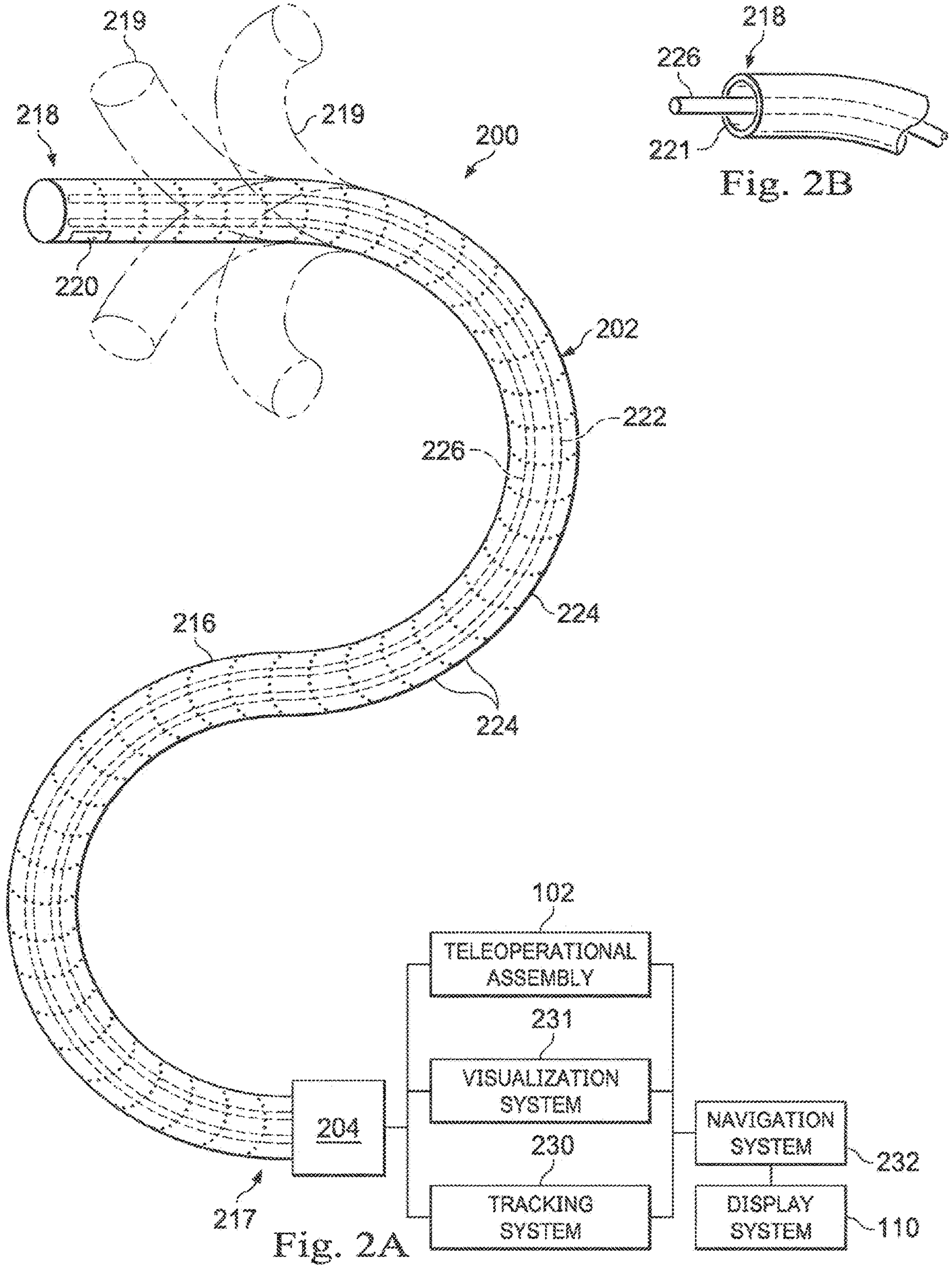
FIG. 2A illustrates a medical instrument system, according to one example of the present disclosure.
FIG. 2B illustrates a distal end of the medical instrument system of FIG. 2A with an extended medical tool, in accordance with embodiments of the present disclosure.

FIG. 2A illustrates a medical instrument system 200, which may be used as the medical instrument system 104 in an image-guided medical procedure performed with teleoperational medical system 100. Alternatively, the medical instrument system 200 may be used for non-teleoperational exploratory procedures or in procedures involving traditional manually operated medical instruments, such as endoscopy. Additionally or alternatively the medical instrument system 200 may be used to gather (i.e., measure) a set of data points corresponding to locations with patient anatomic passageways.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller. The optical fiber of the shape sensor system 222 forms a fiber-optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber-optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as electromagnetic (EM) sensors, positioned along the catheter can be used for shape sensing. Alternatively, a history of data from a positional sensor, such as an EM sensor, on the instrument system during a procedure may be used to represent the shape of the instrument, particularly if an anatomic passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and the shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel 221 (See FIG. 2B) sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In some examples, the medical instrument 226 may be a smaller catheter. In such case, the larger catheter 202 may be referred to as the outer catheter and the smaller catheter inserted into the channel 221 may be referred to as the inner catheter. The inner catheter may also have a channel through which medical instruments such as capture probes, biopsy instruments, ablation probes, and other surgical or diagnostic tools may be inserted.

In various embodiments, the medical instrument(s) 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

In various embodiments, the medical instrument 226 is a biopsy instrument used to remove sample tissue or a sampling of cells from a target anatomic location. The instrument 226 may be advanced from the opening of the channel 221 to perform the procedure and then retracted back into the channel when the procedure is complete. The medical instrument 226 may be removed from the proximal end 217 of the catheter flexible body or from another optional instrument port (not shown) along the flexible body.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also house cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomic systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the operator with real-time position information on the display system 110 for use in the control of the instrument 200. The control system 116 may utilize the position information as feedback for positioning the instrument 200. Various systems for using fiber-optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In the embodiment of FIG. 2A, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

In some examples, the movement of a medical instrument system (e.g., instruments 104, 200) may be directed by one or more manipulator assemblies (e.g., assembly 102) to which the medical instrument is coupled. When using a multiple degree of freedom manipulator assembly to control the medical instrument, the position and orientation of the patient entry passageway relative to the manipulator assembly may be initially unknown. Localizing the position and orientation of the patient entry passageway relative to the manipulator assembly allows the manipulator assembly to direct the instrument into the patient anatomy in a safe and effective manner.

Figure 3:
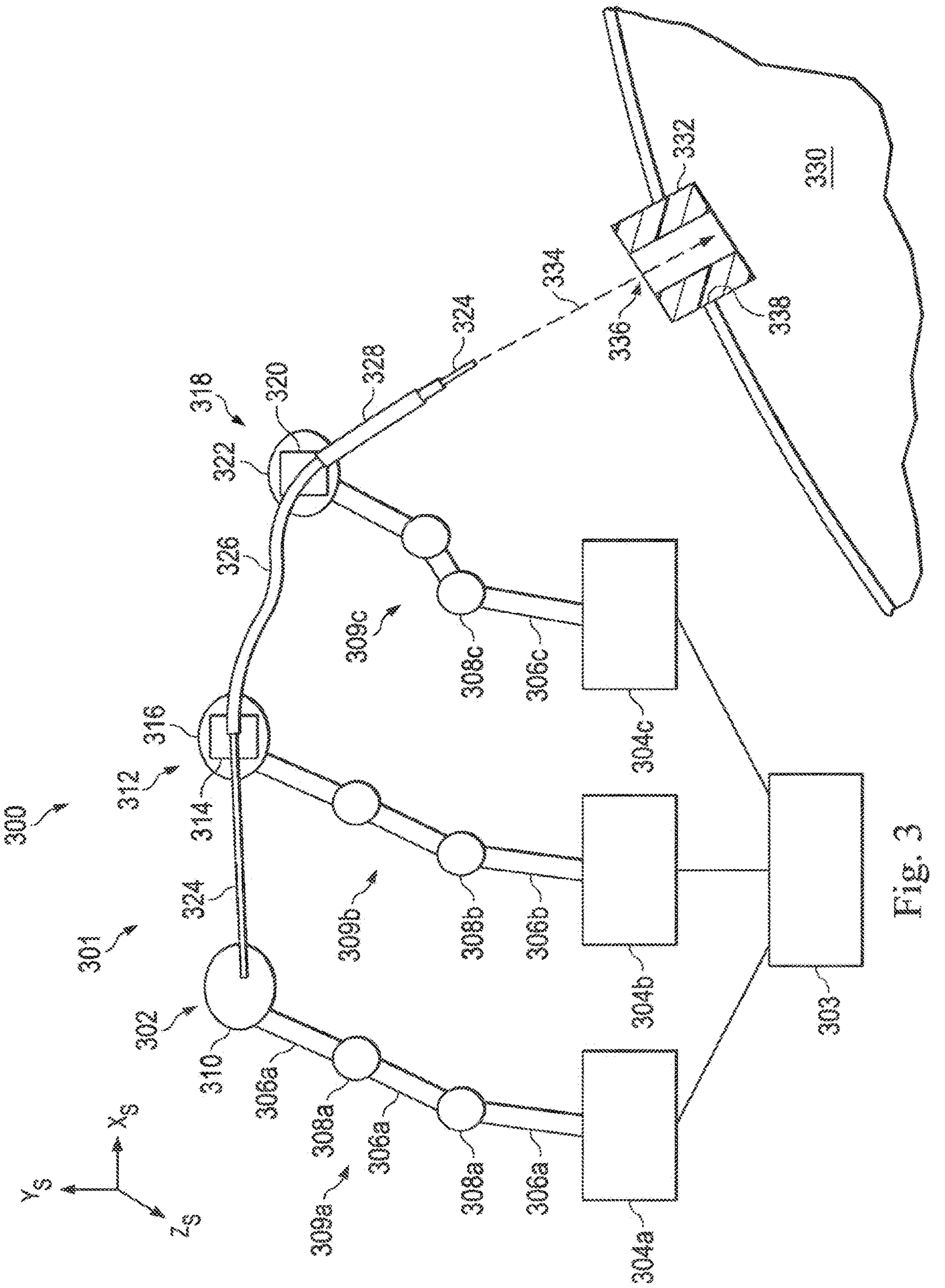
FIG. 3 illustrates a view of a surgical coordinate space that includes a medical instrument system and an entry port through which medical instruments may be inserted, according to one example of the present disclosure.

FIG. 3 illustrates a view of a surgical coordinate space 300 (XS, YS, ZS) that includes a medical instrument system 301. The medical instrument system 301 (e.g., instruments 104, 200) includes an outer catheter 328, an inner catheter 326, and a medical tool 324. According to the present example, each medical instrument is connected to a teleoperative manipulator assembly 302, 312, 318 (e.g. manipulator assembly 102).

The manipulator assembly 302 includes a base 304*a*, a kinematic arm assembly 309*a* that includes a set of links 306*a*, a set of joints 308*a*, and an end mechanism 310. Joints 308*a* may include motors or other actuators to drive movement of the arm 309*a* in one or more degrees of freedom. While the present example illustrates three links 306*a* coupled by two joints 308*a*, other examples may have other numbers of links 306 and joints 308. In some examples, the links may be telescoping links that can extend a predetermined distance. The links are pivotable around the joints so as to move the end mechanism to a desired position within the surgical coordinate system. Some joints may allow rotation in only one plane. Other joints may allow rotation multiple planes.

The combination of links 306*a* and joints 308*a* may provide movement of the end mechanism 310 in six degrees of freedom, which may include three degrees of linear motion (e.g., linear motion along the X, Y, Z Cartesian axes) and three degrees of rotational motion (e.g., rotation about the X, Y, Z Cartesian axes). The arms 309*a* may include wiring, circuitry, and other electronics to convey power and control signals from a control system 303 (e.g. control system 112) to the actuators and to instruments and instrument end effectors coupled to the end mechanism 310. Actuator position sensors such as resolvers, encoders, potentiometers, and other mechanisms may provide sensor data to the control system describing the rotation and orientation of the motor shafts. This position sensor data may be used to determine motion of the objects manipulated by the motors. For example, the joints may have sensors that may determine the rotational position of the joint or determine the angle at which the two links connecting the joint are currently positioned. Additionally, if the links are extendable, then such links may include sensors to determine the distance by which the link is currently extended. In this manner, the position of the end mechanism with respect to the base can be determined based on data from such sensors. Specifically, the control system 303 may process data received by such sensors and determine the position of the end mechanisms 310, 316, 322 with respect to their corresponding bases. Additionally, because the medical tool 324 and catheters 326, 328 may include shape and position sensors as described above, the distal end of each of the medical tool and catheters with respect to the end mechanisms may be known. Thus, the position and orientation of the distal ends of the medical tool and catheters, with respect to each other and a fixed point (e.g., one of the bases 304), within the surgical coordinate space may be determined.

The manipulator assembly 312 includes a base 304*b*, a kinematic arm assembly 309*b* that includes a set of links 306*b*, a set of joints 308*b*, and an end mechanism 316. The manipulator assembly 318 includes a base 304*c*, a kinematic arm assembly 309*c* that includes a set of links 306*c*, a set of joints 308*c*, and an end mechanism 322. The actuation and control of the assemblies 312, 318 may be substantially similar to assembly 302.

The base 304*a*, 304*b*, 304*c* may be portable so that each manipulator assembly can be separately positioned and fixed as desired in a surgical space near a patient. Alternatively, one or more of the manipulator assemblies may be coupled to a cart or other common platform that can be positioned in the surgical space near a patient.

In the example of FIG. 3, the medical tool 324 is connected to the end mechanism 310. Actuation of the tool 324 may be controlled, at least in part, by power and control signals via the end mechanism 310. The inner catheter 326 is connected to the end mechanism 316 by a connector mechanism 314. The connector mechanism 314 may function to guide the medical tool 324 into the inner catheter 326. Actuation of the inner catheter 326 may be controlled, at least in part, by power and control signals via the end mechanism 316. The outer catheter 328 is connected to the end mechanism 322 by a connector mechanism 320. The connector mechanism 320 may function to guide the inner catheter 326 into the outer catheter 328. Actuation of the outer catheter 328 may be controlled, at least in part, by power and control signals via the end mechanism 322. The medical tool 324 is sized and shaped to fit, slide, and rotate within the inner catheter 326. Additionally, the inner catheter 326 is sized and shaped to fit, slide, and rotate within the outer catheter 328. The inner catheter 326 and the outer catheter 320 may be similar to the catheter 202 described above and illustrated in FIG. 2A. The medical tool 324 may be one of a variety of medical tools including a biopsy tool, imaging probe, ablation probe, or other treatment, surgical or diagnostic tool. In alternative embodiments, one or both of the catheters may be omitted or additional manipulator assemblies including additional catheters/tools may be added in a telescoping fashion.

The three end mechanisms 310, 316, 322 may be separately controlled to move the medical tool 324 and catheters 326, 328 as desired. For example, to insert the inner catheter 326 further into the outer catheter 328, the end mechanism 316 may be moved closer to the end mechanism 322. To insert the medical tool 324 further into both the inner catheter 326 and the outer catheter 328, the end mechanism 310 may be moved closer to the end mechanism 316.

The end mechanisms 310, 316, 322 may be moved to insert the distal end of the medical tool 324 and catheters 326, 328 into a patient's body 330. As described above, the tool and catheters may be inserted through a natural or surgically created orifice 338. In either case, the medical instrument is typically inserted through an entry port 332. The entry port 332 may be, for example, an endotracheal tube in the case that the orifice 338 is the patient's mouth. The entry port 332 may be, for example, a trocar cannula in the case that the orifice is a surgically created incision. In any case, it is desirable to know both the entry position 336 through the centerline of the entry port 332 as well as the entry vector 334 through which the medical tool and catheters should be inserted. Any misalignment between the medical tool or catheter and the entry port during insertion could cause motion of the entry port resulting in harm to the patient. Thus entry position and entry vector information can be useful to provide safe and effective entry of instruments into the patient's body 330.

Initially, the entry position 336 and the entry vector 334 in both the surgical coordinate space and relative to the manipulator assemblies 302, 312, 318 may be unknown. Determination of the entry position 336 and entry vector 334 of the entry port 332 in the surgical coordinate space and/or with respect to the manipulator assemblies may be accomplished through a variety of techniques. As will be described in further detail below, the entry position 336 and entry vector 334 may be determined using alignment component such as EM sensors, optical sensors, fiber-optic shape sensors, and other mechanisms. Additionally, various methods may be used to provide the control system 303 with the entry position 336 and entry vector 334 before the surgical procedure begins.

Figure 4:
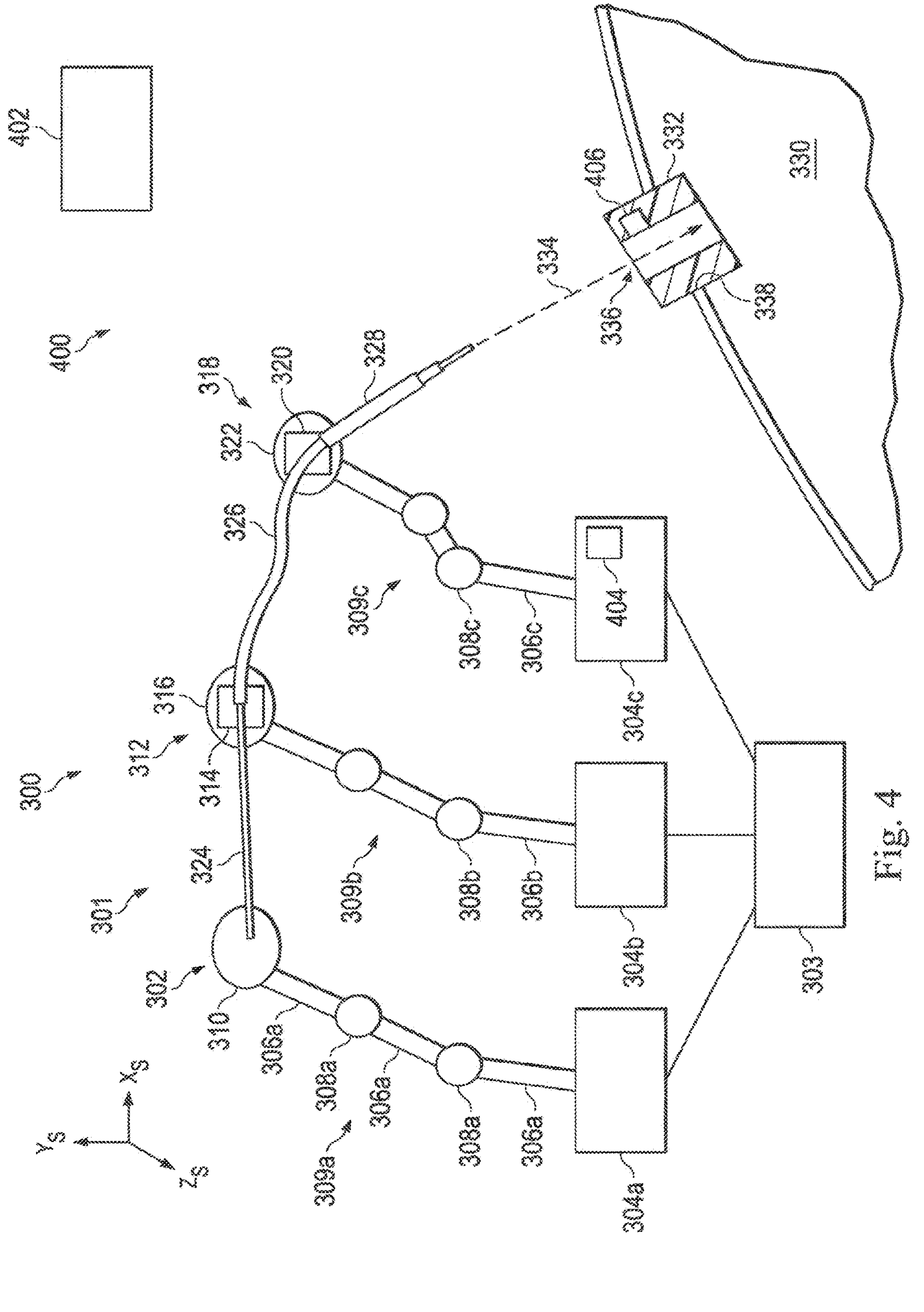
FIG. 4 illustrates an electromagnetic sensor system that uses electromagnetic sensors to determine the position and orientation of the entry port, according to one example of the present disclosure.

FIG. 4 illustrates a position sensor system 400 that uses alignment components including position sensors 404, 406 to determine the position and orientation of the entry port 332. In this example, the alignment components may be position sensors such as EM sensors, but other types of position sensors may be suitable. According to the present example, one or more EM sensors 406 are located (e.g., fixedly coupled) on the entry port 332. Additionally, one or more EM sensors 404 are located on the manipulator assembly 318 at a known location relative to the end mechanism 322. The known location of the EM sensor relative to the end mechanism may be known based upon a kinematic chain or sensors in the arm. In one example, the sensor 404 may be located on the base 304*c*. An EM emitter 402 is used to determine the position of each of the EM sensors 404, 406 with respect to the EM emitter 402. The EM emitter may be at a fixed or known location in the surgical coordinate space and may be in communication with the control system 303. The control system 303 may process position data received by the emitter to determine the positions and orientations of the EM sensors 404, 406 with respect to the EM emitter 402 in the surgical coordinate space. By knowing the position of the EM sensor 404 in the surgical coordinate space, the position of the end mechanism 322 is known (kinematically or based upon sensors). Additionally, the position and orientation of the actuated distal end of the medical instrument system 301 can be known, for example, based on the control signals used to steer the distal end or other optical fiber shape sensors and/or position sensors within the medical instrument system 301. Additionally, by knowing the position and orientation of the entry port (through EM sensor 406) with respect to the EM emitter 402, the position of the entry port 332 with respect to the distal end of the medical instrument system may be known.

Optionally, additional EM sensors may be located on each of the manipulator assemblies 302, 312 to determine the position and orientation of the respective end mechanisms 310, 316. Alternatively, if the manipulator assemblies 302, 312 are coupled to a common platform with the manipulator assembly 302, with known kinematic relationships between the assemblies, the EM sensor 404 on manipulator 318 may be sufficient to determine the position and orientation of the end mechanisms 310, 316.

As described above, an EM sensor 404, 406 may include one or more conductive coils that may be subjected to an electromagnetic field that is generated by the EM emitter 402. Each coil of the EM sensor system 400 then produces an induced electrical signal having characteristics that depend on the position and orientation of the coil relative to the electromagnetic field generated by the EM emitter 402. The EM sensor system 400 may be configured and positioned to measure six degrees of freedom, e.g., three position coordinates X, Y, Z and three orientation angles indicating pitch, yaw, and roll of a base point or to measure five degrees of freedom, e.g., three position coordinates X, Y, Z and two orientation angles indicating pitch and yaw of a base point.

In some examples, the EM emitter 402 may be located on one of the manipulator assemblies in place of the EM sensor 404. In such case, the EM emitter 402 is able to determine the position and orientation of the EM sensor 406 and thus can determine the position and orientation of the entry port 332 with respect to the manipulator assembly. Like the EM sensor 404, the EM emitter 402 may be located at any point on any one of the manipulator assemblies 302, 312, 318.

Figure 5A:
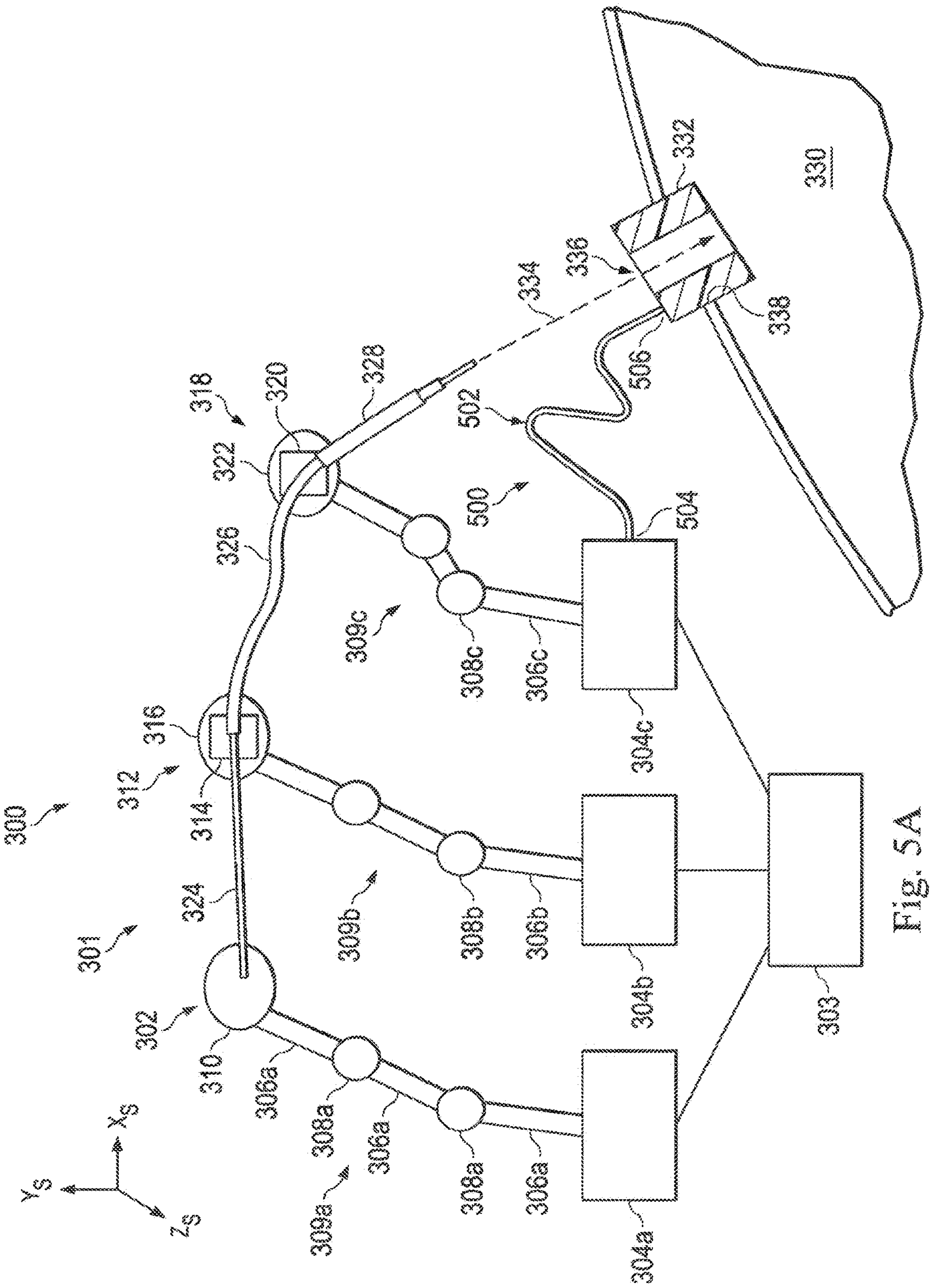
FIG. 5A illustrates a fiber-optic shape sensor system that uses a fiber-optic shape sensor to determine the position and orientation of the entry port, according to one example of the present disclosure.

FIG. 5A illustrates an alignment component, including a fiber-optic shape sensor system 500 that is used to determine the position and orientation of the entry port. According to the present example, the fiber-optic shape sensor system 500 includes a fiber-optic shape sensor 504 extending between the manipulator assembly 318 and the entry port 332. The fiber-optic shape sensor 504 can be similar in function to sensors such as shape sensor 222, previously described. Specifically, a proximal portion 504 of the fiber-optic shape sensor 502 is connected to the base 304*c* of the manipulator assembly 318. Additionally, a distal portion 506 of the fiber-optic shape sensor 502 is connected to the entry port 332. In this example, the base 304*c* will be referred to as the reference fixture and the entry port 332 will be referred to as the target fixture.

In one example, the fiber-optic sensor system 500 includes an interrogation system (not shown) that is positioned at the reference fixture. In operation, the interrogation system generates light and detects returning light to determine the current shape of the fiber-optic shape sensor 502. The interrogation system may then create data representing the detected light. This data may be analyzed by the control system 303 to determine the position and orientation of the target fixture (i.e. the entry port 332). Because the reference fixture 304*c* has a fixed or known position in the surgical reference frame, combination with the shape of the sensor between the proximal portion 504 and distal portion 506 provides the position and orientation of the entry port 332 located at the distal portion 506 in the surgical reference frame. As described above, the position and orientation of the instrument system 301 with respect to the manipulator assembly 318 (including the reference fixture 304*c*) is known or trackable relative to the reference fixture 304*c* in the surgical reference frame. Thus, the position and orientation of the instrument system 301 with respect to the entry port 332 can be known and tracked.

The fiber-optic shape sensor 502 may include one or more optical cores. In some cases, the fiber-optic shape sensor may include one or more optical fibers, each optical fiber having one or more optical cores. As described above, the core may include Fiber Bragg Gratings to provide strain measurements in one or more dimensions. In other alternatives, sensors employing other strain sensing techniques may be suitable.

Figure 5B:
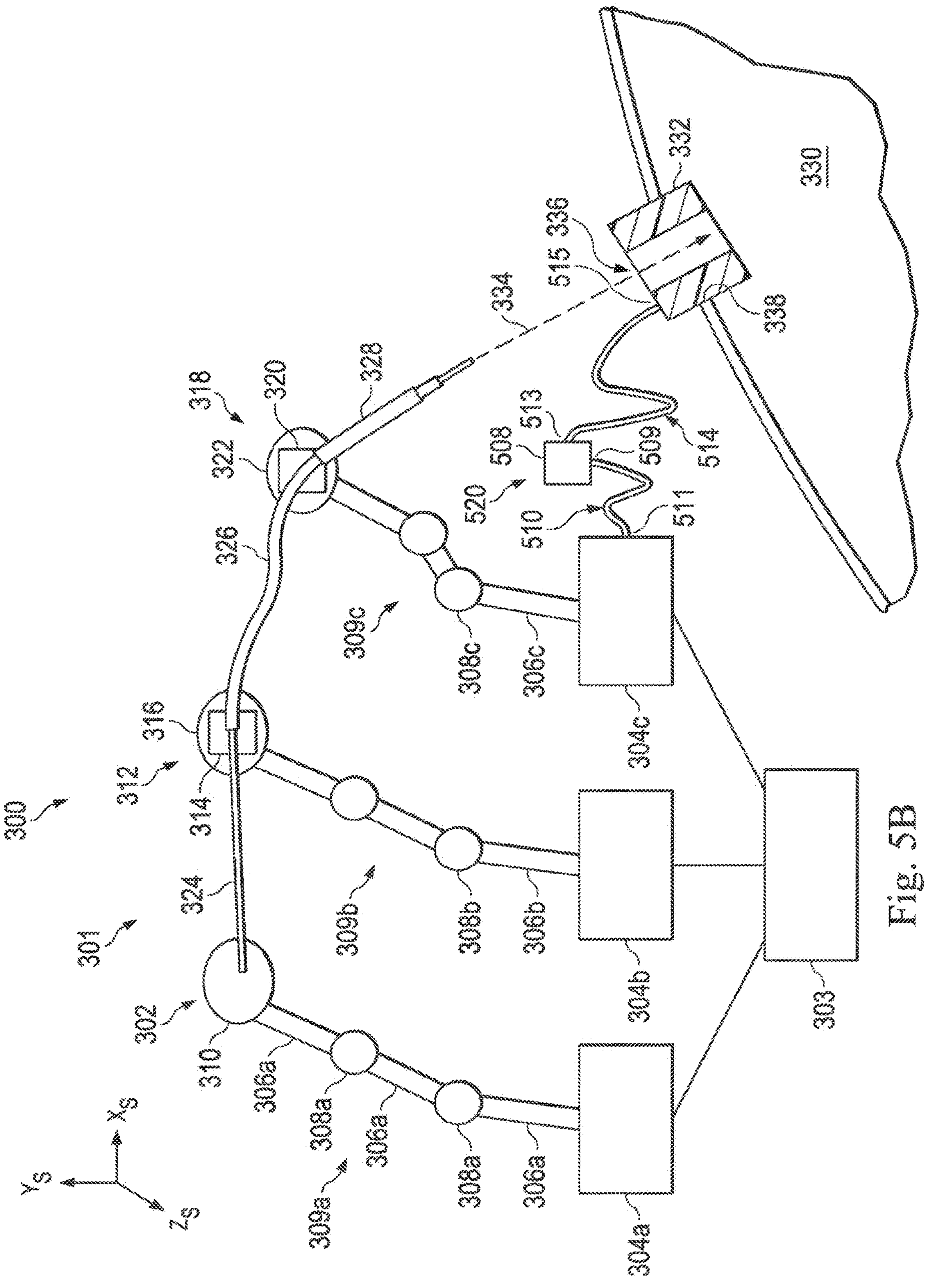
FIG. 5B illustrates a fiber-optic shape sensor system that uses multiple fiber-optic shape sensors to determine the position and orientation of the entry port, according to one example of principles described herein.

FIG. 5B illustrates a fiber-optic shape sensor system 520 that uses alignment components including two fiber-optic shape sensors 510, 514 to determine the position and orientation of the entry port 332. In the present example, both the base 304*c* of the manipulator assembly 318 and the entry port 302 are used as target fixtures while a separate point is used as the reference fixture 508. The reference fixture 508 has a known or fixed location in the surgical coordinate space. A first portion 509 of the fiber-optic shape sensor 510 is connected to the reference fixture 508, and a second portion 511 of the fiber-optic shape sensor 510 is connected to the base 304*c*. In alternative embodiments, other portions of the manipulator assembly 318 may be used as the target fixture. Additionally, a first portion 513 of the fiber-optic shape sensor 514 is connected to the reference fixture 508 and a second portion 515 of the fiber-optic shape sensor 514 is connected to the entry port 332. All connections may be fixed couplings. The reference fixture 508 may include an interrogation system that transmits light along each of the fiber-optic shape sensors 510, 514. The interrogation system then detects returned light from the fiber-optic shape sensors 510, 514 to determine the shapes of the sensors 510, 514 in the surgical coordinate space. Using the shape information from sensor 514, the position and orientation of the entry port 332 (i.e., the position and orientation of portion 515) in the surgical coordinate space may be determined. In some examples, the fiber-optic shape sensor 514 may be extended through the length of the entry port 332, and the measured shape within the entry port may be used to determine the entry port vector 334. Similarly, the shape information from sensor 510 is used to determine the position and orientation of the base 304*c* (i.e., the position and orientation of the portion 511), in the surgical coordinate space. As described above, the position and orientation of the instrument system 301 with respect to the manipulator assembly 318 (including the base 304*c*) is known or trackable. Thus, the position and orientation of the instrument system 301 with respect to the entry port 332 can be known and tracked.

Figure 6A:
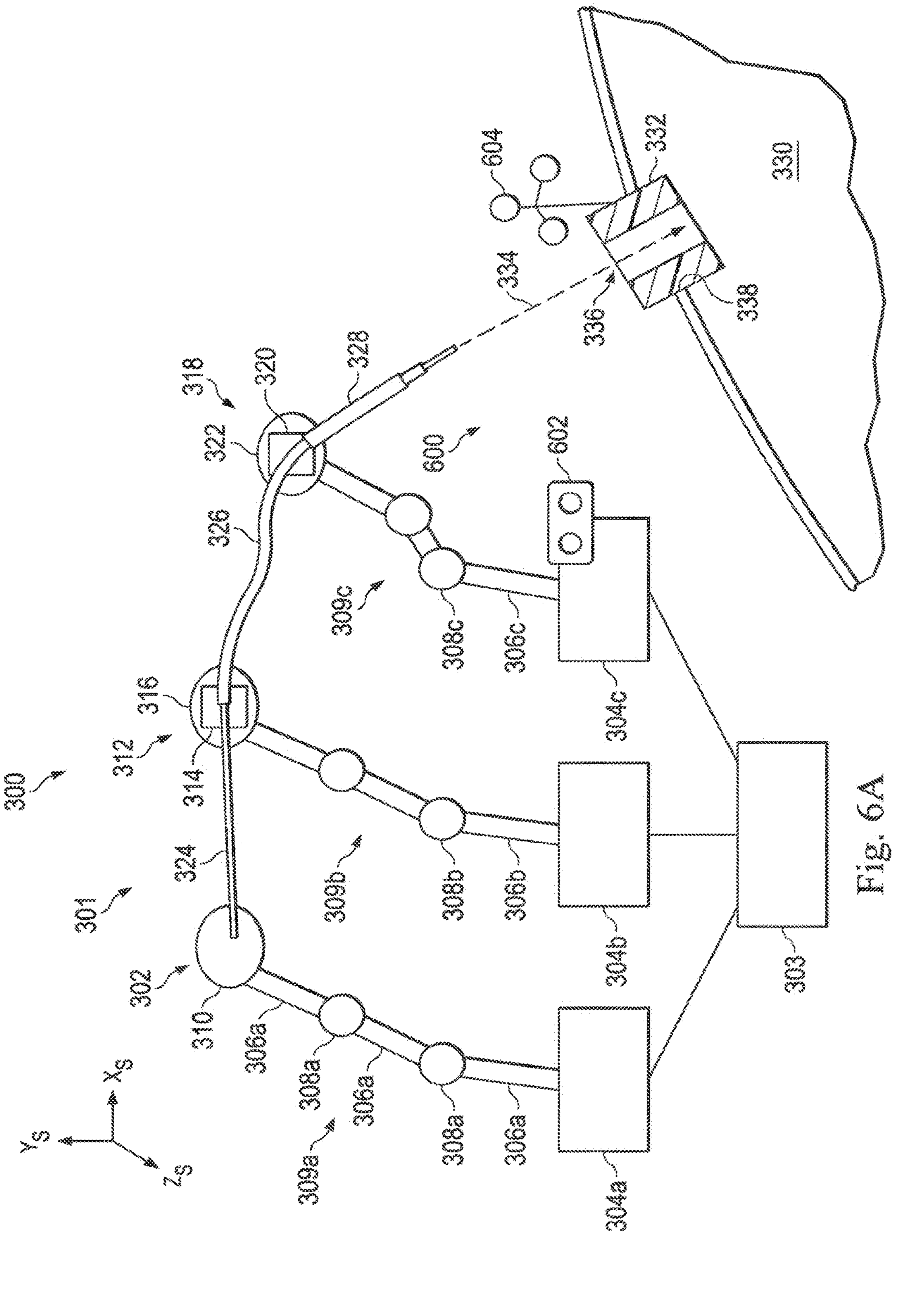
FIG. 6A illustrates an optical tracking system that uses an optical marker and an optical tracker to determine the position and orientation of the entry port, according to one example of the present disclosure.

FIG. 6A illustrates an optical tracking system 600 that may be used to determine the position and orientation of the entry port 332. According to the present example, the optical tracking system 600 includes alignment components including an optical tracker 602 connected to the manipulator assembly 318 and optical marker 604 connected to the entry port 332. The optical tracker 602 may include a pair of cameras capable of emitting infrared rays and receiving infrared rays reflected by the optical tracker. The optical marker 604 may include special reflectors positioned on reference arrays. The stereo-optic nature of the optical tracker 602 allows it to determine the location optical marker 604 with respect to the position of the optical tracker 602 in the surgical coordinate space. As described above, the position and orientation of the instrument system 301 with respect to the manipulator assembly 318 (to which the optical tracker 602 is coupled) is known or trackable. Thus, the position and orientation of the instrument system 301 with respect to the entry port 332 can be known and tracked.

In this example, the optical marker 604 is a passive marker that may include spherical, retro-reflective markers to reflect the infrared light emitted by illuminators on the optical tracker 602. In alternative systems, the optical tracker may be an active infrared-emitting marker that is activated by an electrical signal. Further descriptions of optical tracking systems are provided, for example, in U.S. Pat. No. 6,288,783, filed Oct. 28, 1999, disclosing, "System for determining spatial position and/or orientation of one or more objects," which is incorporated by reference herein in its entirety. As described in this embodiment, the optical marker 604 may be fixedly coupled to the entry port 332 such that the movement of the medical instrument relative to and independent of the optical marker 604.

Figure 6B:
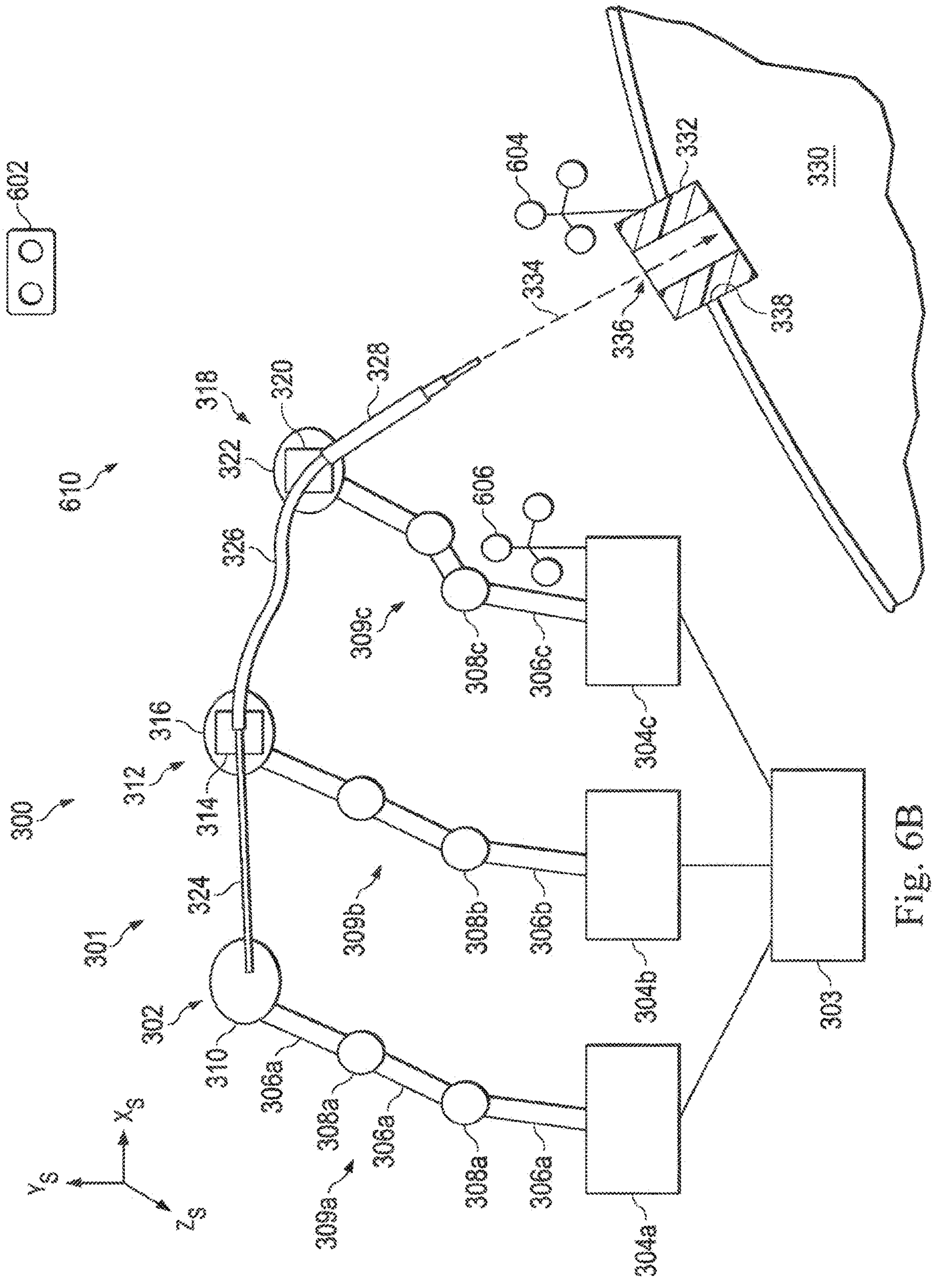
FIG. 6B illustrates an optical tracking system that uses an optical tracker and multiple optical markers to determine the position and orientation of the entry port, according to one example of the present disclosure.

FIG. 6B illustrates an optical system 610 that uses alignment components including an optical tracker 602 and multiple optical markers 604, 606 to determine the position and orientation of the entry port 332. According to the present example, the optical tracker 602 is placed at a fixed or known location within the surgical coordinate space. Additionally, an optical marker 604 is placed on the entry port and an optical marker 606 is placed on the manipulator assembly 318. The optical tracker 602 tracks the position and orientation of the markers 604, 606. Therefore, the position and orientation of the entry port 332 and the manipulator 318, relative to the optical tracker 602 is known. By knowing both the position of the manipulator assembly 318 with respect to the optical tracker 602 and position of the entry port 332 with respect to the optical tracker 602, the position of the entry port 332 with respect to the manipulator assembly 318 may be determined and tracked.

Figure 7:
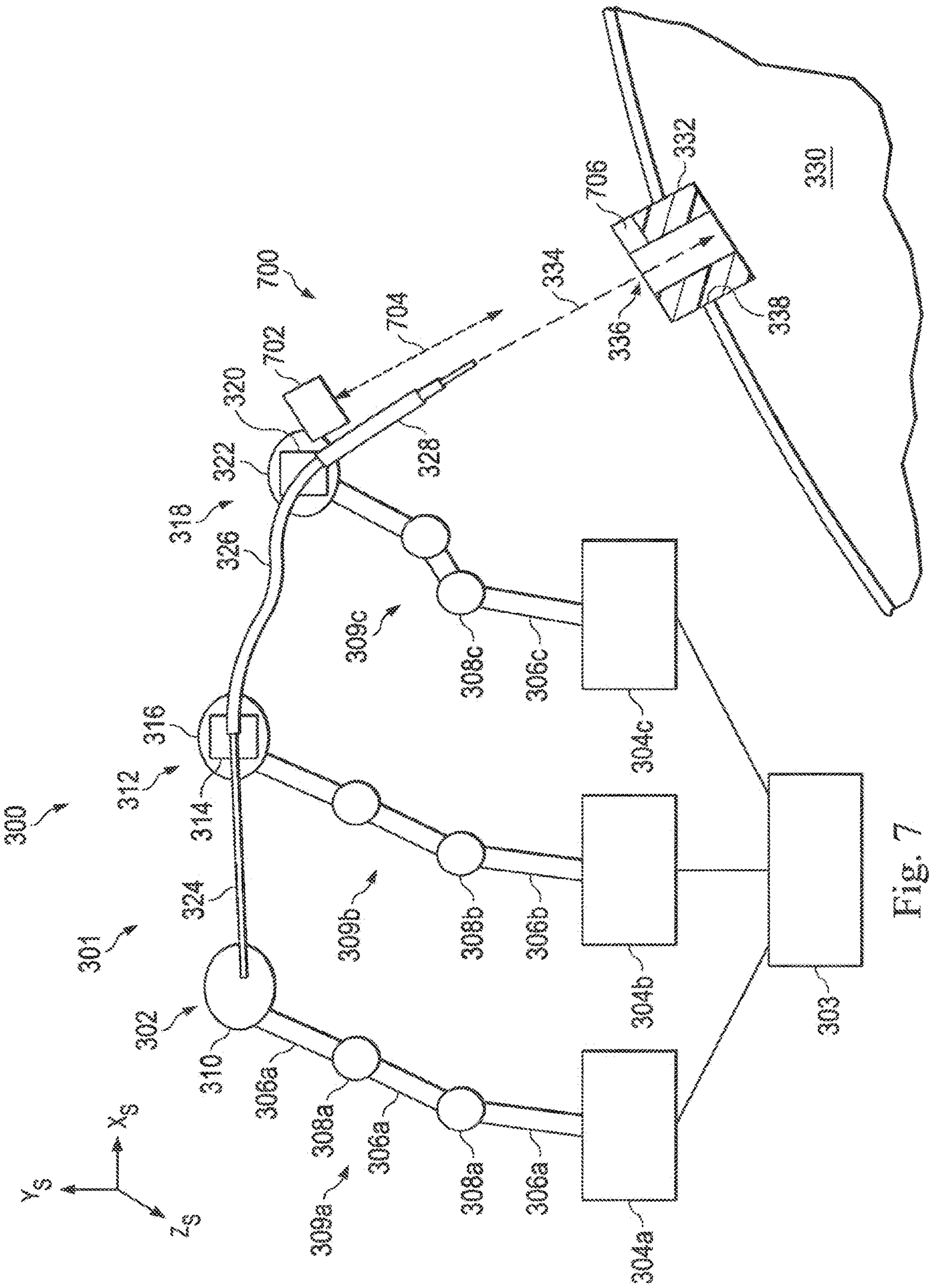
FIG. 7 illustrates a laser system that uses a laser to determine the position and orientation of the entry port, according to one example of the present disclosure.

FIG. 7 illustrates a laser system 700 that is used to determine the position and orientation of the entry port 332. According to the present example, the laser system 700 uses alignment components including a laser emitter 702 that includes a reflection sensor and a reflector mechanism 706. The laser emitter 702 is secured to the end mechanism 322. Additionally, the reflector mechanism 706 is secured to the entry port 332. The reflector mechanism 706 includes reflectors designed to reflect a laser beam 704 emitted by the laser emitter 702. The end mechanism 322 may be moved, while emitting the laser beam 704 until the laser beam 704 is be reflected back to the reflection sensor on the laser emitter 702. The sensor on the laser emitter 702 (in communication with the control system 303) may be able to measure characteristics of the reflected laser beam to determine the distance between the laser emitter 702 and the entry port 332. Knowing this information, the position of the entry port 332 with respect to the medical instrument system 301 may be known. Additionally, when the reflected beam 704 is detected, the laser beam direction corresponds to the direction of the entry vector 334. Thus, the position and entry vector of the entry port 332 are known with respect to the manipulator 318 and, consequently, the instrument system 301. In alternative embodiments, the reflector mechanism may be omitted and a user may visually align the emitted laser beam with the entry port 332 to determine the entry vector. As described in this embodiment, the reflector mechanism 706 may be fixedly coupled to the entry port 332 such that the movement of the medical instrument relative to and independent of the reflector mechanism 706.

Figure 8:
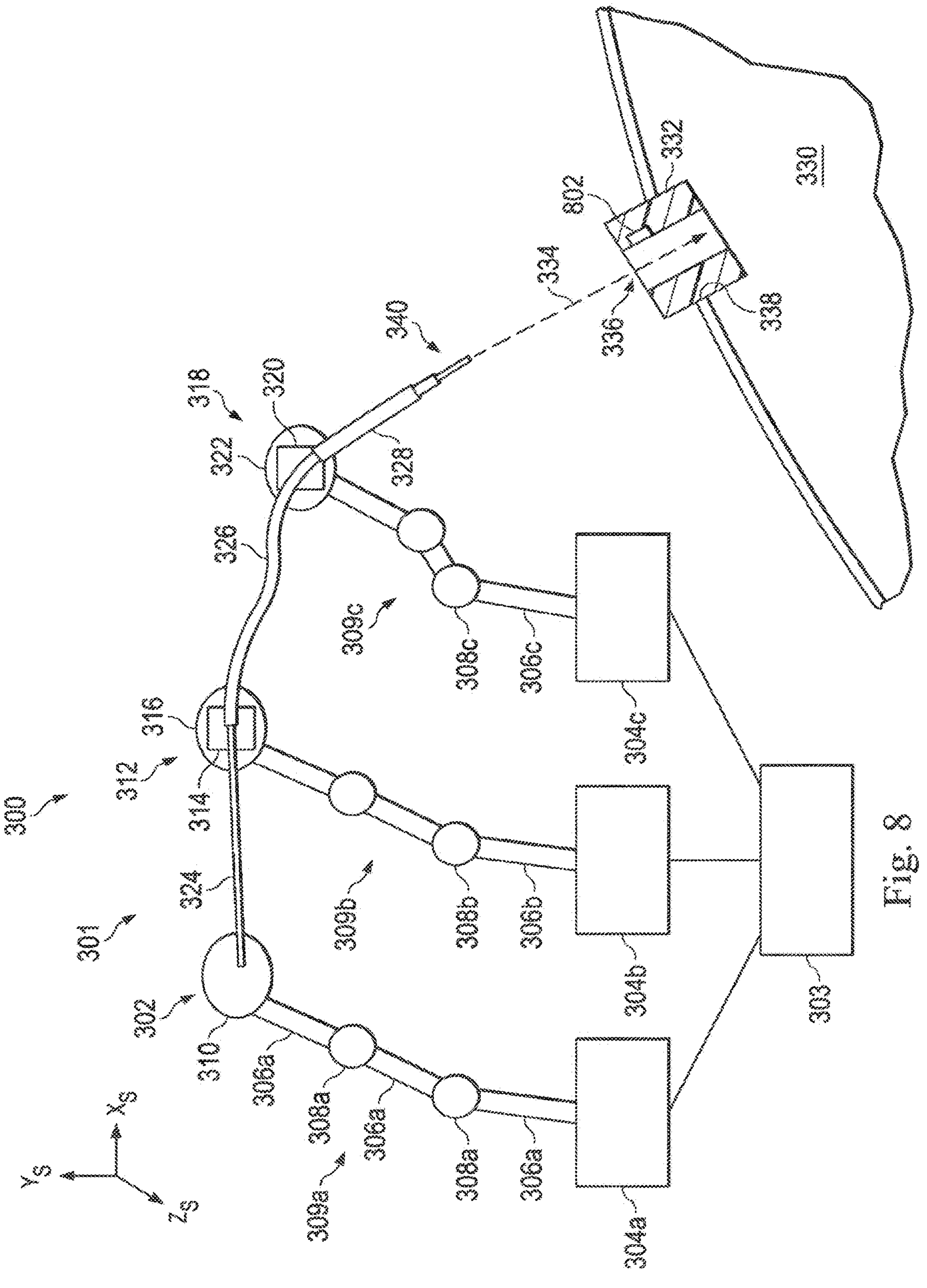
FIG. 8 illustrates a technique for placing the distal end of the medical instrument system at the entry port to determine the position and orientation of the entry port, according to one example of the present disclosure.

FIG. 8 illustrates a technique for using the medical instrument 301 to determine the position and orientation of the entry port 332, prior to the initiation of the surgical procedure. In this example, a distal end 340 of the medical instrument system is touched to the entry port 332 to determine the position and orientation of the entry port 332. According to the present example, the manipulator assemblies 302, 312, 318 are manipulated to position the distal end 340 of the medical instrument system 301 at the entry port 332. In some examples, the distal end of the medical instrument system 340 may be at least partially inserted into the entry port 332. In alternative examples, the medical instrument 301 can be touched to a plurality of points along the length of the entry port or at a point on the opening of the entry port and a point at the base of the entry port such that the entry angle can be calculated based on multiple points. The control system 303 may then use the various sensors on the medical instruments system to determine the current position and orientation of the distal end of the medical instrument system 301 when the medical instrument 301 is making contact with the entry port at the desired location. For example, a shape sensor extending through the instrument system 301 to the distal end 340 is referenced to the surgical coordinate frame and is queried to determine a shape of the instrument and, consequently, the position and orientation of the distal end 340 in the surgical reference frame. The control system 303 may then record this position and orientation as the position and orientation of the entry port 332 in the surgical coordinate system. The medical instrument system 301 may then be removed from the entry port 332 until the surgical procedure is ready to begin.

In some examples, alignment of the position and orientation of the distal end of the medical instrument system 301 to the position and orientation of the entry port 332 may be triggered when an operator visually observes that the medical instrument system 301 is appropriately positioned at the entry port 332. In this example, one or more of the manipulator assemblies can be visually positioned in an orientation where the medical instrument is aligned with the entry port robotically or manually with the motors in the joints served off. The one or more manipulator assemblies may then be robotically controlled to travel along a straight line trajectory aligned with the entry vector and the trajectory is recorded based on the known position of the distal end of the medical instrument via sensors and/or kinematic calculations as previously described.

In the more specific example referring back to FIG. 3, manipulator assembly 318 and 312 can both be positioned manually or robotically such outer catheter 328 and inner catheter 326 are both approximately aligned with the entry vector. The catheters 328, 326 can be coaxially positioned providing alignment of both manipulator assemblies 318, 312 with the entry vector 334. Alternatively, manipulator assembly 318 may be oriented to align the connector mechanism 320 in line with the entry point and entry vector, then the manipulator assembly can be locked in position and the connector mechanism 320 can be rotated to better align the outer catheter 328 with the entry vector 334. The manipulator 312 can then be manually or automatically positioned such that the inner catheter 326 is positioned within the outer catheter 328. The entry vector 334 can be calculated between points on the manipulator assemblies 318 and 312, for instance the entry vector can be calculated from the inner catheter connector mechanism 314 to the outer catheter connector mechanism 320.

In other examples, the entry port 332 may include an alignment component including an indicator 802 that is used to detect that the medical instrument system 301 is positioned at or partially within the entry port 332 in order to automatically trigger the localization of the entry port. In one example, the indicator 802 is a temperature anomaly device that produces a temperature anomaly such as a relatively cold temperature or a relatively hot temperature. Because the fiber-optic shape sensors in the medical instrument systems are sensitive to changes in temperature, the fiber-optic shape sensors along the medical instrument system may detect the temperature anomaly. Detection of the temperature anomaly may thus trigger the localization. In some embodiments, the shape sensor may be sufficiently sensitive to body temperature that entry into the patient anatomy provides sufficient heat to trigger the localization.

Figure 9:
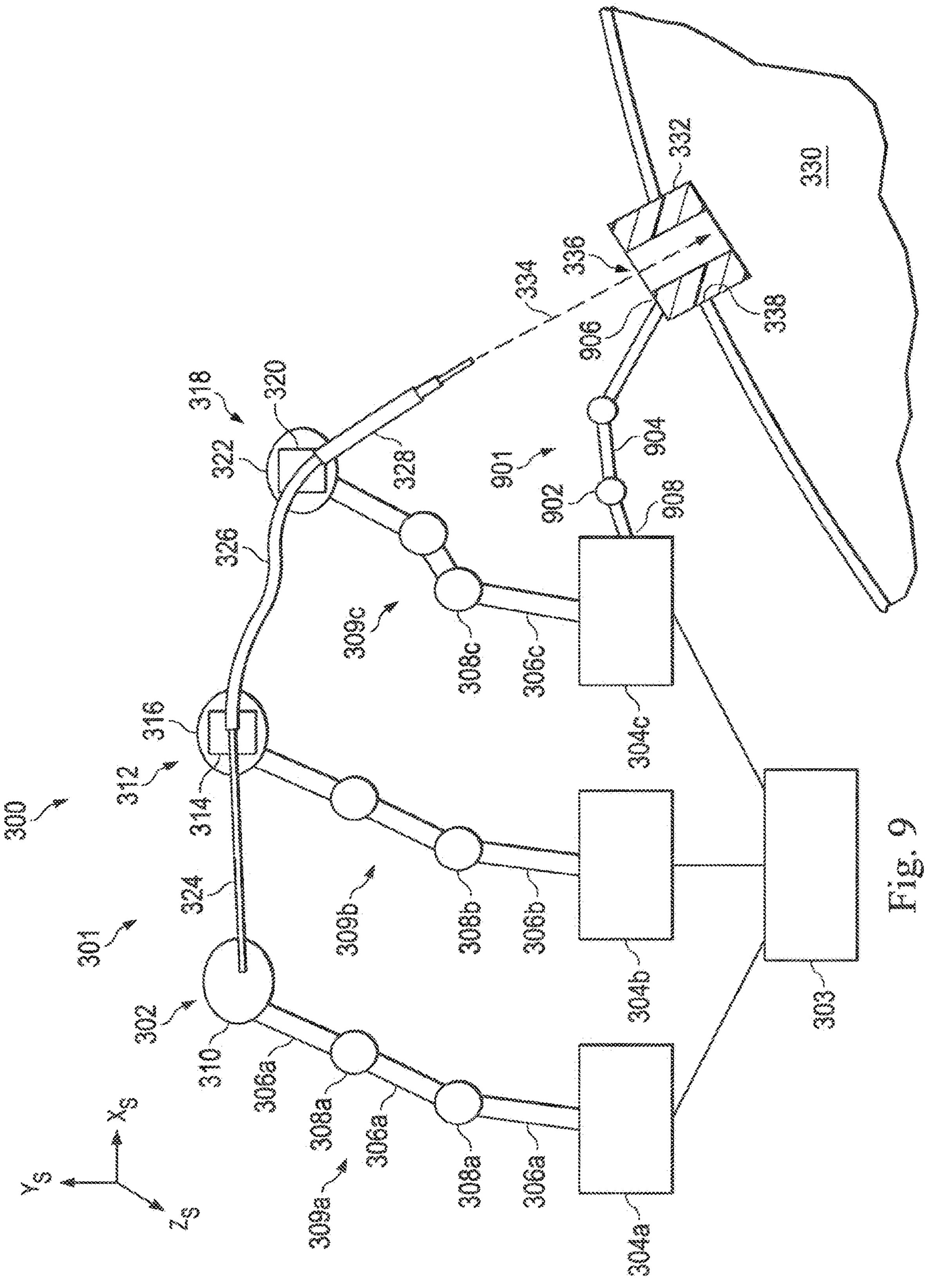
FIG. 9 illustrates a sensed kinematic structure that is used to determine the position and orientation of the entry port, according to one example of the present disclosure.

FIG. 9 illustrates an alignment component including a sensed kinematic structure 901 that is used to determine a position of the entry port 332. According to the present example, the sensed kinematic structure 902 includes a set of links 904 and a set of joints 902. Similar to the joints 308 and links 306 of the manipulator assemblies, the links in a foreign the joints 902 may include sensors that together produce data that can be analyzed to determine the point in the surgical coordinate space of a distal end 906 with respect to the proximal end 908. Thus, with proximal end 908 attached to the manipulator assembly 318 and the distal end 906 attached to the entry port 332, the position and orientation of the entry port with respect to the manipulator assembly 318 may be known. In some cases, the ends may be attached manually by an operator after the patient is positioned. In some examples, after the ends are attached, the control system may register the position and orientation of the entry port. At this stage of the procedure, because the position and orientation of the entry port 332 is now known, and is unlikely to change during operation, the sensed kinematic structure 902 may be removed.

Figure 10:
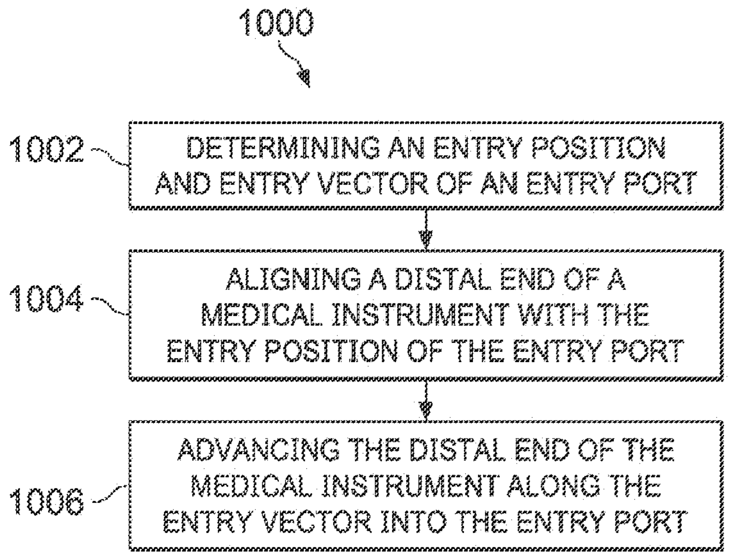
FIG. 10 is a flowchart showing an illustrative method for localizing an entry point, according to one example of the present disclosure.

FIG. 10 is a flowchart showing an illustrative method 1000 for localizing an entry port. The method 1000 is illustrated in FIG. 10 as a set of operations or processes 1002-1006. Not all of the illustrated processes 1002-1006 may be performed in all embodiments of method 1000. Additionally, one or more processes that are not expressly illustrated in FIG. 7 may be included before, after, in between, or as part of the processes 1002-1006. In some embodiments, one or more of the processes may be implemented, at least in part, in the form of executable code stored on non-transitory, tangible, machine-readable media that when run by one or more processors (e.g., the processors of control system 112 or 303) may cause the one or more processors to perform one or more of the processes.

According to the present example, the method includes a step 1002 for determining a position (e.g., 336, FIG. 3) and entry vector (e.g., 334, FIG. 3) of an entry port (e.g., 332, FIG. 3). This may be done through a variety of means as described above. For example, various alignment components such as EM sensors, fiber optic shape sensors, and optical tracking systems may be used to determine the position and orientation of the entry port. As described above, the determination of the entry position and entry vector may occur while the medical instrument is removed from or otherwise external to the entry port. The method further includes a step 1004 for aligning a distal end of a medical instrument (e.g., 301, FIG. 3) with the entry position of the entry port. This may be done by controlling the manipulator assemblies (e.g., 302, 312, 318, FIG. 3) and steering the distal end of the instrument system 301 to move the medical instrument into alignment. The method further includes a step 1006 for advancing the distal end of the medical instrument along the entry vector into the entry port. Again, this may be done by controlling the manipulator assemblies to move the medical instrument as desired.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a non-transitory processor readable storage medium or device, including any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method performed by a computing system, comprising:

determining an entry position and entry vector of an entry port in a surgical coordinate space, the entry port providing a passageway for insertion of a first medical instrument into a patient's body, wherein the determining of the entry position and entry vector occurs while the first medical instrument is external to the entry port;

positioning the first medical instrument based on the entry position and the entry vector of the entry port; and advancing a distal end of the first medical instrument into the entry port.

2. The method of claim 1, wherein the first medical instrument is coupled to a teleoperational manipulator and wherein positioning the first medical instrument includes positioning the teleoperational manipulator to align the distal end of the first medical instrument with the entry vector.

3. The method of claim 1 wherein advancing the distal end of the first medical instrument is along the entry vector into the entry port.

4. The method of claim 1, wherein determining the entry position and entry vector of the entry port is based on determining a position of a first alignment component in the surgical coordinate space, the first alignment component coupled to the entry port.

5. The method of claim 4, wherein determining the entry vector of the entry port is based on determining a pose of the first alignment component in the surgical coordinate space.

6. The method of claim 4, wherein the first alignment component comprises a first position sensor.

7. The method of claim 6, wherein the first position sensor comprises a first electromagnetic sensor and wherein determining the position of the first alignment component includes sensing the position of the first alignment component with an electromagnetic emitter that is registered to a manipulator mechanism in the surgical coordinate space, wherein the manipulator mechanism is connected to the first medical instrument.

8. The method of claim 7, wherein determining the entry vector includes sensing positions of both the first electromagnetic sensor and a second electromagnetic sensor to determine a relative position between the first and second electromagnetic sensors.

9. The method of claim 4, wherein the first alignment component comprises a first electromagnetic sensor and wherein determining the entry position includes determining a position of a second alignment component comprising a second electromagnetic sensor, the second alignment component coupled to a manipulator mechanism connected to the first medical instrument.

10. The method of claim 4, wherein the first alignment component comprises a first portion of a fiber-optic shape sensor and wherein determining the position of the first alignment component includes determining a position of the first portion of the fiber-optic shape sensor, wherein a second portion of the fiber-optic shape sensor is coupled to a manipulator mechanism connected to the first medical instrument.

11. The method of claim 4, wherein the first alignment component comprises a portion of a first fiber-optic shape sensor and wherein determining the position of the first alignment component includes determining a position of the portion of the first fiber-optic shape sensor relative to a reference fixture and includes determining a position of a portion of a second fiber-optic shape sensor relative to the reference fixture, the portion of the second fiber-optic shape sensor coupled to a manipulator mechanism connected to the first medical instrument.

12. The method of claim 4, wherein the first alignment component comprises an optical marker and wherein determining the position of the first alignment component includes tracking the optical marker with an optical tracker coupled to a manipulator mechanism connected to the first medical instrument.

13. The method of claim 4, wherein the first alignment component comprises a first optical marker and wherein determining the position of the first alignment component includes tracking the first optical marker and a second optical marker coupled to a manipulator mechanism connected to the first medical instrument.

14. The method of claim 4, wherein the first alignment component comprises a first end of a sensed kinematic structure and wherein determining the position of the first alignment component includes determining the position of the first end of the sensed kinematic structure, wherein a second end of the sensed kinematic structure is coupled to a manipulator mechanism connected to the first medical instrument.

15. The method of claim 1, wherein determining the entry position and entry vector of the entry port comprises aiming a laser at the entry port, the laser being coupled to a manipulator mechanism connected to the first medical instrument.

16. The method of claim 1, wherein determining the entry position and entry vector of the entry port comprises:

positioning the distal end of the first medical instrument at and aligned with the entry port and recording a position and orientation of the distal end of the first medical instrument.

17. The method of claim 1, further comprising:

aligning a second medical instrument with the entry port;

determining a position of the second medical instrument; and determining the entry vector based on relative positions of the first and second medical instruments.

18. The method of claim 17, wherein the second medical instrument is adapted to fit inside and pass through the first medical instrument.

19. A teleoperative system, comprising:

a teleoperational manipulator;

a medical instrument coupled to and movable by the teleoperational manipulator;

an entry port providing a passageway for insertion of the medical instrument into a patient body; and a control system configured to:

determine an entry position and entry vector of the entry port in a surgical coordinate space while the medical instrument is external to the entry port;

position the medical instrument based on the entry position and the entry vector of the entry port; and advance a distal end of the medical instrument into the entry port.

20. The teleoperative system of claim 19, wherein the control system is configured to determine the entry position and the entry vector of the entry port by determining a position of an alignment component in the surgical coordinate space, the alignment component coupled to the entry port.

* * * * *